United States Patent [19]

Ostern

[11] 4,047,989
[45] Sept. 13, 1977

[54] METHOD FOR THE RECOVERY OF BLASTING OIL FROM EFFLUENTS FROM THE PRODUCTION OF NITROGLYCERINE-CONTAINING EXPLOSIVES

[75] Inventor: Sverre Ludvik Ostern, Ski, Norway

[73] Assignee: Dyno Industrier A.S., Oslo, Norway

[21] Appl. No.: 687,649

[22] Filed: May 18, 1976

[30] Foreign Application Priority Data

May 23, 1975 Norway .................................. 751834

[51] Int. Cl.$^2$ ............................................. C06B 23/00
[52] U.S. Cl. ................................... 149/109.6; 149/88; 149/101; 149/104; 260/645
[58] Field of Search ................ 149/109.6, 101.88, 104; 260/645

[56] References Cited

U.S. PATENT DOCUMENTS 3,778,320  12/1973  Yosim et al. ...................... 149/101 X
3,975,452  8/1976  Mayer et al. .......................... 260/645

Primary Examiner—Stephen J. Lechert, Jr.
Attorney, Agent, or Firm—Wenderoth, Lind & Ponack

[57] ABSTRACT

Blasting oil contained in the effluent from the production of explosives containing nitroglycerine is recovered by extracting with nitroaromatics which make part of the final explosive, the resulting extract being used completely in the explosive production. Residues of nitroaromatics may be removed from the purified effluent by means of an extraction liquid being sparely water-soluble, such as toluene or xylene or a mixture thereof.

3 Claims, 1 Drawing Figure

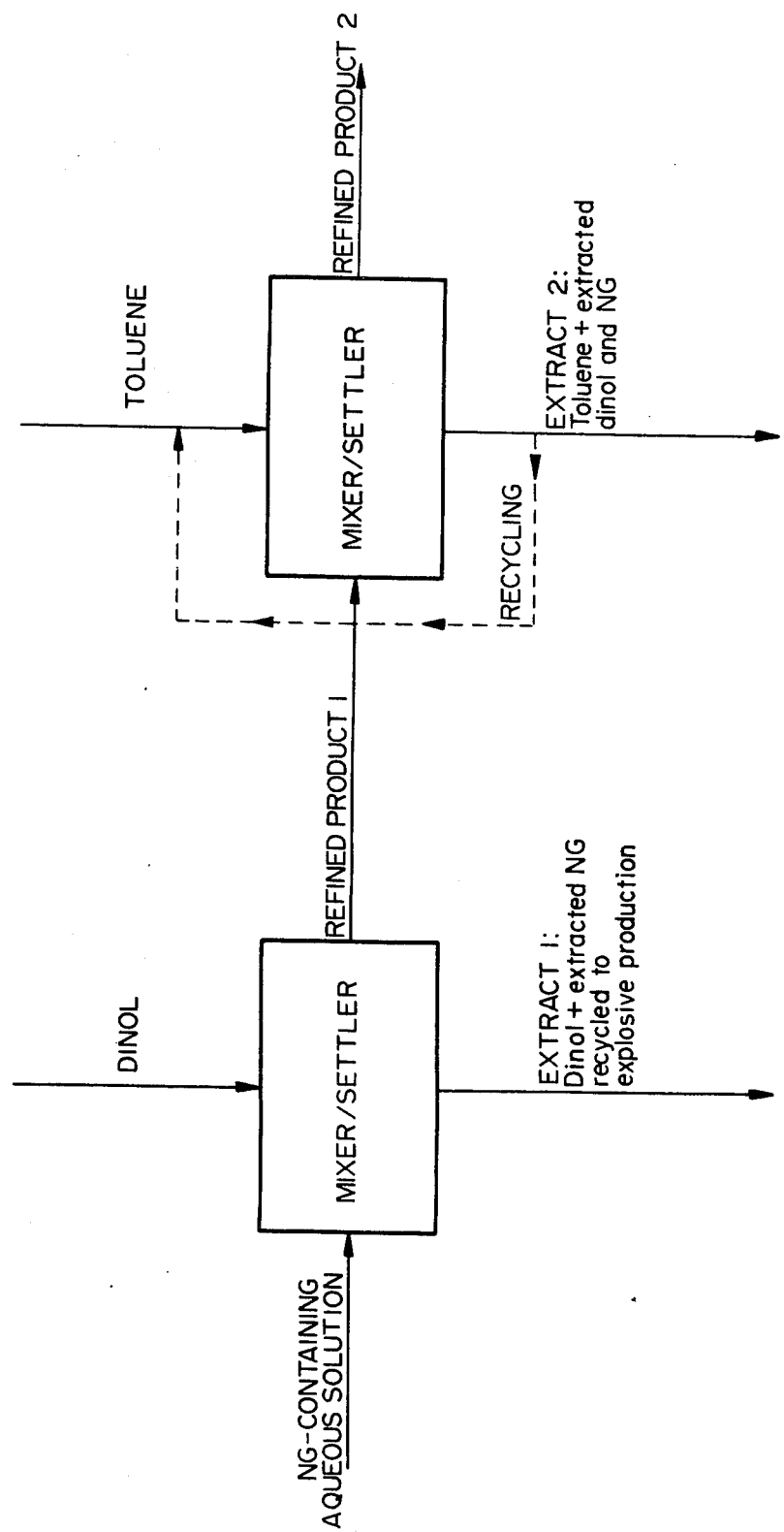

METHOD FOR THE RECOVERY OF BLASTING OIL FROM EFFLUENTS FROM THE PRODUCTION OF NITROGLYCERINE-CONTAINING EXPLOSIVES

Heavily loaded recipients are continuously loaded with nitrate-containing effluents from explosive factories. This is due to the fact that, up to now, no safe methods have been available for the treatment of aqueous solutions containing blasting oil. Blasting oil, herein also termed NG, is short for glycol dinitrate and glycerine trinitrate as well as for mixtures thereof in various proportions. The main discard of nitrates from some explosive factories originate from the process for producing NG wherein $HNO_3$, dissolved in NG, has to be neutralized and washed out. In those processes in which the neutralization is carried out by washing in a solution of $Na_2CO_3$, the used wash water will contain $NaNO_3$, $NaHCO_3$ and NG. As seen from an environmental and economical point of view, it is desirable to recover the said chemicals from the effluent, so that they can be reused, preferably in the explosive manufacture. The hazard connected with the treatment of NG-containing solutions, however, is that NG may precipitate from the solution. NG is known to be very sensitive to mechanical stresses and may also be chemically unstable. Thus, an incorrect treatment of NG-containing solutions may have the effect that precipitated NG may detonate. Several methods for eliminating NG from aqueous solutions could be figured out, such as, e.g., by means of charcoal, ion exchangers or liquid/liquid extraction.

The said methods have in common that one will obtain NG-containing products which, from a safety point of view are undesired for the further treatment aiming at recovery or destruction. In case it would be possible, in a safe way, to discard or burn the said products, the recipient would moreover be provided with a further waste product, viz., the chemicals used for eliminating NG from the solutions.

The present invention aims at removing NG from solutions having been contacted with NG, in order that the said solutions can be further treated without any NG-explosion hazard. Such NG-containing solutions may, e.g., be effluents from the washing process for NG, or water from the ejector transport of NG.

Accordingly, the invention provides a method for the recovery of blasting oil (NG) from effluents in the manufacture of NG-containing explosives, said method being characterized therein that the nitroaromatic which forms part of the formulation of the final explosive, is passed through an apparatus wherein an effluent containing blasting oil is extracted by means of said nitroaromatic, whereafter said blasting oil-containing extract in its entirety is utilized for the preparation of the final explosive. In case it is also desired to remove nitroaromatics from the purified effluent, one may carry out a further liquid/liquid extraction by means of an extraction liquid that is sparely soluble in water, such as, e.g., toluene or xylene or a mixture thereof.

As indicated, NG is removed by means of a liquid/liquid extraction with a nitroaromatic. As the extracting agent is used either nitrated toluene, nitrated xylene or a mixture thereof. A variety of such nitrated compounds are commercially available. The one that is most commonly used is dinitrotoluene, called dinol, having varying proportions of the isomers and varying contents of trinitrotoluene. There are also dinol grades available that contain nitrated xylene.

The mentioned nitrated compounds are generally used as raw materials in the preparation of NG-containing explosives. This means that the extract, consisting of the extracting agent and extracted NG, can be recycled completely to the explosive production. In this respect it is referred to the enclosed flow sheet.

The refined product, viz., the extracted effluent, thereafter can be trated further without any explosion hazard, in order that the recovery of dissolved nitrates or other chemicals may be achieved.

The chemicals dissolved in the effluent may then be removed completely from the recepient. For instance, the nitrates may be utilized for the production of different types of explosives, as nitrogen additives in biological cleaning plants, or as artificial fertilizers in the agriculture. In case a higher purity is desired for the chemicals to be recovered, a further liquid/liquid extraction is carried out for the removal of the residues of nitroaromatics in the refined product. As extracting agents heavily water soluble liquids may be used, which liquids are at the same time capable of extracting the residues of nitroaromatics in the refined product. Examples of such extracting agents are toluene and xylene, as well as mixtures thereof.

In case toluene or xylene is employed as the extracting agent, the extract may be recycled completely to the process for the preparation of corresponding nitroaromatics.

By means of a combination of liquid/liquid extraction of NG-containing solutions, first by means of nitroaromatics and then with toluene or xylene or a mixture thereof, the following advantages, among others, may be obtained:

All chemicals may be recovered and reused, e.g., in the explosive manufacture, this being of value seen from an economical and environmental point of view.

It is not necessary to change existing recipes because the substances that are recycled are already ingredients of the most usual NG-containing explosives.

Essential advantages with respect to safety precautions are achieved because the handling of the refined product does not imply any explosion hazard. Moreover, the nitroaromatics will phlegmatize extracted NG so that the recycling back to the explosive manufacture will be relatively safe.

EXAMPLE

Table 1 refers to six typical extraction series performed in a Mixer/settler apparatus and a Pulse column apparatus.

It was started with an NG-containing effluent from the NG-wash process, herein termed "wash water." The following three types of nitroaromatics were tested as extraction liquids for the removal of NG:

a common dinitrotoluene commercial product, called "Dinol G." Melting point = 51° C (Extraction series 2)

dinitrotoluene comprising 40 percent dinitroxylene, calculated on the mixture, termed "Dinol X." Melting point = 30° C. (Extraction series 1, 4, 5 and 6)

dinitrotoluene to which has been added 35 percent trinitrotoluene, calculated on the mixture, termed "Dinol T." Melting point = 26° C. (Extraction series 3)

As it appears from the Table, all three nitroaromatics reduced the NG-contents of the wash water rather effectively, viz., down to 0.51 - 0.87 percent of the original NG-content.

The tests showed also that a one-stage Pulse column gave about the same extraction degree as a two-stage Mixer/settler.

In order to avoid the formation of crudes in the interphases, i.e., an accumulation of visible impurities in the interphases, during the extraction process with dinol it was necessary to maintain the temperature about 10° C higher than the melting point of the dinol used.

The Refined Product 1, i.e., wash water extracted by means of a nitroaromatic contained residues of the nitroaromatic in charge, besides minor amounts of NG. In order to remove the residues of nitroaromatics from the Refined Product 1 a further extraction was carried out by means of the following extraction agents:

Toluene (Extraction series Nos. 1, 2, 3 and 5)
"Solvesso 150" (Extraction series No. 4)
Xylene (Extraction series No. 6).

Some data for Solvesso 150 have been summarized in the following Table 2.

TABLE 1

| Extraction series No. | Apparatus | Wash water NG mg/l | Dinol grade | Wash water/ dinol ratio | Refined Product 1 NG mg/l | Refined Product 1 Dinol mg/l | Apparatus | Extraction liquid | Ratio Refined Product 1/ Extr. liquid | Refined Prod. 2 NG mg/l | Refined Prod. 2 Dinol mg/l |
|---|---|---|---|---|---|---|---|---|---|---|---|
| 1 | 2 stage Mixer/settler | 4710 | Dinol X | 5:1 | 24 | 416 | 2 stage Mixer/settler | Toluene | 5:1 | 4 | 1 |
| 2 | 2 stage Mixer/settler | 5680 | Dinol G | 5:1 | 39 | 415 | 2 stage Mixer/settler | Toluene | 5:1 | 12 | 9 |
| 3 | 2 stage Mixer/settler | 5680 | Dinol T | 5:1 | 32 | 545 | 2 stage Mixer/settler | Toluene | 5:1 | 13 | 22 |
| 4 | 2 stage Mixer/settler | 5260 | Dinol X | 5:1 | 46 | 355 | 2 stage Mixer/settler | "Solvesso" | 5:1 | 38 | 8 |
| 5 | 1 stage Pulse/column | 4340 | Dinol X | 5:1 | 35 | 468 | 1 stage Pulse/column | Toluene | 5:1 | 8 | 7 |
| 6 | 2 stage Mixer/settler | 5170 | Dinol X | 5:1 | 22 | 416 | 2 stage Mixer/settler | Xylene | 5:1 | 10 | 4 |

TABLE 2

| Data for "Solvesso 150" | |
|---|---|
| Content of aromatics: | 97 % |
| Boiling point range: | 192–207° C. |
| Flame point: | 66° C. |
| Density at 15° C: | 0.89 |

The amount of nitroaromatics in Refined Product 1, thus, was reduced rather effectively. The contents of NG was reduced further, so that the contents of NG in wash water in total was reduced to 0.08 - 0.23 percent of the original content. The experimental data refer to a specific phase ratio between wash water and extracting agent, viz., the ratio 5 : 1. This does not necessarily mean that the phase ratio 5 : 1 is the most favourable in the extracting process.

In case the number of stages is increased in the apparatus, it will be possible to reduce the content of NG further.

Regarding the nitroaromatics the extraction effect is reduced at NG-contents higher than 2 percent in the extract. Thus, it will hardly be economical to recycle the extract when the NG-content of aqueous solutions lies close to 0.4 percent and the phase ratio aqueous solution/nitroaromatics being 5 : 1.

The Refined Product 1 comprises relatively small amounts of nitroaromatics. Provided the phase ratio aqueous solution/toluene is 5 : 1, it is, thus, possible to recycle toluene about 50 times without reducing the extraction degree substantially.

I claim:

1. A method for recovering blasting oil selected from the group consisting of glycol dinitrate, glycerine trinitrate and mixtures thereof from an effluent resulting from the production of blasting oil-containing explosives which comprises extracting the blasting oil from the effluent with a liquid nitroaromatic in an extraction apparatus, said nitroaromatic liquid being a component used in the blasting oil-containing explosive such that the blasting oil-nitroaromatic extract can be utilized for the preparation of the final explosive.

2. A method according to claim 1, wherein the nitroaromatic is selected from the group consisting of nitrated toluene, nitrated xylene and mixtures thereof.

3. A method according to claim 1, wherein the blasting oil-nitroaromatic extract is further extracted with a liquid selected from the group consisting of toluene, xylene and mixtures thereof to remove the nitroaromatics therefrom.

* * * * *